(12) United States Patent
Schwyn et al.

(10) Patent No.: US 8,051,720 B2
(45) Date of Patent: Nov. 8, 2011

(54) METHOD AND DEVICE FOR MEASURING THE LOCAL MECHANICAL RESISTANCE OF A POROUS BODY

(75) Inventors: Ronald Schwyn, Davos Glaris (CH); Markus Haenni, Davos Platz (CH); Norbert Suhm, Davos Wolfgang (CH)

(73) Assignee: AO Technology AG, Chur (CH)

( * ) Notice: Subject to any disclaimer, the term of this patent is extended or adjusted under 35 U.S.C. 154(b) by 500 days.

(21) Appl. No.: 12/159,659

(22) PCT Filed: Oct. 31, 2006

(86) PCT No.: PCT/CH2006/000611
§ 371 (c)(1),
(2), (4) Date: Jun. 30, 2008

(87) PCT Pub. No.: WO2008/052367
PCT Pub. Date: May 8, 2008

(65) Prior Publication Data
US 2008/0300510 A1    Dec. 4, 2008

(51) Int. Cl.
*G01N 3/00*    (2006.01)
(52) U.S. Cl. ........................................ 73/760
(58) Field of Classification Search ............ 73/760
See application file for complete search history.

(56) References Cited

U.S. PATENT DOCUMENTS

| 5,360,448 | A | * | 11/1994 | Thramann .................. 606/60 |
| 6,549,814 | B1 | * | 4/2003 | Strutz et al. .................. 607/137 |
| 6,663,562 | B2 | * | 12/2003 | Chang .......................... 600/219 |
| 6,690,166 | B2 | | 2/2004 | Ni et al. |
| 6,763,257 | B1 | * | 7/2004 | Rosholm et al. ............. 600/407 |
| 7,080,562 | B2 | * | 7/2006 | Knowles et al. ............. 73/818 |
| 7,107,883 | B2 | * | 9/2006 | Casutt .......................... 81/467 |
| 2003/0057947 | A1 | | 3/2003 | Ni et al. |
| 2006/0149263 | A1 | * | 7/2006 | Newcomb et al. ........... 606/73 |
| 2006/0224088 | A1 | | 10/2006 | Roche |

FOREIGN PATENT DOCUMENTS

| DE | 33 30 802 A1 | 3/1985 |
| DE | 100 18 769 A1 | 10/2001 |
| EP | 1 491 294 A1 | 12/2004 |
| GB | 2 313 916 A | 12/1997 |
| JP | 2000-245736 | 9/2000 |

* cited by examiner

*Primary Examiner* — Lisa Caputo
*Assistant Examiner* — Octavia Davis
(74) *Attorney, Agent, or Firm* — Rankin, Hill & Clark LLP

(57) ABSTRACT

Method and device for determining the local mechanical resistance inside of a porous body having a variable density and/or porosity, in particular inside of a porous bone structure comprising the following steps:
  selecting a site of said porous body destined to receive a fixation element, in particular a screw or a bone implant;
  drilling a hole into said porous body; and
  measuring a mechanical parameter of the porous structure surrounding said drilled hole by inserting a suitable tool (1) into said drill hole.

22 Claims, 3 Drawing Sheets

METHOD AND DEVICE FOR MEASURING THE LOCAL MECHANICAL RESISTANCE OF A POROUS BODY

FIELD OF THE INVENTION

The invention relates to a method for measuring the local mechanical resistance inside of a porous body having a variable density and/or porosity, in particular inside of a porous bone structure, that includes (A) selecting a site of said porous body destined to receive a fixation element, in particular a screw or a bone implant, (B) drilling a hole into said porous body and (C) measuring a mechanical parameter of the porous structure surrounding said drilled hole by inserting a suitable tool into said drill hole. The invention also relates to a device for measuring the local mechanical resistance inside of a porous body that includes (A) a tool with a shank designed in such a manner that it is insertable into a hole artificially drilled into said body and that is capable of exerting a torsional force on said porous structure surrounding said drilled hole, (B) a measuring unit for determining the elastic or destructive properties of said porous body generated by the torsion force of said tool in said porous body, and (C) displaying means for displaying the properties of said porous body determined by the measuring unit.

DESCRIPTION OF THE PRIOR ART

Various methods for the characterization of bone porosity are known in the art. Japanese patent publication JP2000245736 describes an osteoporosis diagnostic device by means of microwaves. U.S. Pat. No. 6,763,257 ROSHOLM ET AL. discloses a method of estimating the bone quality by using radiogrammetry and U.S. Patent Appl. No. US 2003/0057947 NI ET AL. describes a NMR technology for the characterization of bone porosities. All these known methods are non-invasive.

The quality/strength of the fixation of any kind of fixation elements in a porous structure with variable density/porosity is highly depending on the local quality where the fixation device is inserted. Global data of said density/porosity does not really help to determine the quality of the fixation as by virtue the fixation element might be placed in an area of low or high density/porosity which might be quite different from the average density/porosity. Measuring of the hardness on the surface does not help either as the outer wall on that structure most likely is of different density or porosity and might be very thin not providing enough material for a good fixation.

In the German Laid Open Publication DE 100 18 769 MORLOCK a method and an instrument is disclosed for the intraoperative determination of bone quality. However, this method is limited in its applicability to the femur into which a femoral stem of a hip joint is going to be implanted. To this effect the neck of the femur is cut through and it is then possible to impact the tip of measuring instrument into the spongiosa and to measure the force of a spring which is compressed by the impacting force. There are several drawbacks of this known method, namely:

- it is not reliable because the tip of the measuring instrument is not guided;
- only one value can be measured (static measurement) at a specific site; if several measurement are taken they are not interrelated;
- the spongiosa may undergo more damage by the measurement than by the implant alone.

SUMMARY OF THE INVENTION

It is an object of the invention to provide a device which is capable of determining and/or predicting the local quality of a porous body, in particular of a porous bone structure.

The invention solves this problem using a method that includes (A) selecting a site of said porous body destined to receive a fixation element, in particular a screw or a bone implant, (B) drilling a hole into said porous body and (C) measuring a mechanical parameter of the porous structure surrounding said drilled hole by inserting a suitable tool into said drill hole, and a device that includes (A) a tool with a shank designed in such a manner that it is insertable into a hole artificially drilled into said body and that is capable of exerting a torsional force on said porous structure surrounding said drilled hole, (B) a measuring unit for determining the elastic or destructive properties of said porous body generated by the torsion force of said tool in said porous body, and (C) displaying means for displaying the properties of said porous body determined by the measuring unit.

An important advantage of the method and the device according to the invention is that it allows to determine the mechanical resistance in a second part hidden by a first part of a porous body, which is only reachable through the drill hole crossing the first part and entering the second part and can't be measured directly by tools/devices according to prior art.

The tool and device according to the invention is particularly useful in situations where bone screws are to be implanted into an osteoporotic bone.

In a preferred embodiment said measuring is performed dynamically such allowing the advantage that compared to measuring a single value at a maximum a dynamic measurement permits to record and store a set of continuously or stepwise measured data which can be subsequently plotted as a graph.

In a further embodiment said mechanical parameter is the mechanical resistance of the porous structure due to its deformation.

In another embodiment said mechanical parameter is the mechanical resistance of the porous structure caused by the torsional force applied through rotating a suitable tool.

In still a further embodiment said torsional force is measured for obtaining free axial rotation of a suitable tool in said porous structure.

In yet another embodiment the twisting angle of the tool is measured which is obtained by applying a pre-selectable maximum torsional force. A typical value for such a maximum torsional force is 8 Nm such allowing the advantage that the measurement of the mechanical resistance of the porous structure is performed in an almost nondestructive manner.

Again another embodiment further comprises the steps of:
1) comparing said measured properties with standardized values of said properties obtained with porous structures of different density of porosity;
2) displaying the result of the comparison of said measured versus said standardized properties.

In a further embodiment said fixation element is a longitudinal fixation element and preferably a bone screw.

In another embodiment said drilling of a hole is performed in a direction essentially coaxial to the desired position of said longitudinal fixation element. The advantage thus achieved is that the measurement can be performed e.g. via the same surgical path as the implant will subsequently be inserted.

In still a further embodiment said measuring is effected by inserting said tool into said hole and impacting it into said surrounding porous structure.

In yet another embodiment said porous body is a surf board or part of a boat hull or any structure with foam like parts.

In again a further embodiment said porous body is a porous bone structure and said longitudinal fixation element is a bone implant.

In a further embodiment said hole is drilled until a depth which corresponds at least to the thickness of the cortical bone at said site of the porous bone structure.

In still a further embodiment the drilling of said hole is part of the preparation for the insertion of said longitudinal fixation element, preferably in the form of a predrilling of a center bore.

In another embodiment several distinctive measurements are taken to get averaged results with standard deviation for higher accuracy.

In yet another embodiment several sites are selected for obtaining several values of the local mechanical resistance at this various sites. The advantage achieved is that averaged results with standard deviation for higher accuracy can be obtained.

In a further embodiment the mechanical resistance is measured in the wall of said drilled hole at one or more distinctive locations.

In yet a further embodiment the mechanical resistance is measured by pushing a blade into the bottom of the drilled hole to a certain distance and measuring the twisting moment needed to turn the blade once around.

In another embodiment a certain number of stepwise measurements are taken in one or in a number n>1 drill holes.

In still another embodiment said stepwise measurements are taken by alternately predrilling to the depth planned for the next measurement and taking said measurement.

In a further embodiment said stepwise measurements are guided by a wire set coaxial to the central axis of the planned drill hole before the first predrilling, deep enough to stay in place during the whole measurements or even until the fixation element is inserted.

In yet a further embodiment said stepwise measurements are used to calculate averaged results with standard deviation for each drill hole and/or in total for higher accuracy.

In another embodiment the results measured in said 1 to n drill holes are used to calculate the over all quality/strength of the fixation construct using a number m fixation elements where $m \leq n$.

In still another embodiment said 1-m fixation elements are used to fix one or more additional construction elements to the porous structure.

In a further embodiment the measured values are retrievably stored in a microprocessing unit. By this means the advantage is achieved that a data processing, e.g. averaging of the measured values and reading of the results can be performed in-situ.

In still a further embodiment the measured values retrievably stored in the microprocessing unit are transferred to a computer for further processing. Herewith, the advantage can be achieved that the computer can be provided with other parameters defining the bone quality, e.g. image based and/or physical such improving the predictability of the resistance against, e.g. stripping threads holding a bone screw or the like.

In another embodiment the hole in said porous structure is drilled at an angle between 45° and 90°, preferably between 60° and 90° with respect to the surface of the porous structure.

In a preferred embodiment of the device according to the invention said tool and said measuring unit are incorporated in a single handheld instrument.

In a further embodiment said tool is a blade for measuring the torsional force necessary for obtaining free axial rotation of said blade in said porous structure from its impacted position.

In still a further embodiment said tool is a blade for measuring the angle of rotation of the tool obtained by applying a pre-selectable maximum torsional force. This allows the advantage that the measurement of the mechanical resistance of the porous structure is performed in an almost nondestructive manner In another embodiment the measuring unit is provided with a microprocessing unit allowing to retrievably store the measured values.

In yet another embodiment the microprocessing unit is suitably programmed for retrievably storing continuously measured values. This embodiment allows the advantage that dynamic measurements can be taken and that complete graphs or plots can be stored instead of individual values as known from prior art.

In a further embodiment the measuring unit is detachable from the tool in such manner that the microprocessing unit is electrically connectable to a computer in order to transfer the measured data to the computer. Thus, the advantage is achievable that only the device but not the computer and other means connected thereto must be sterilized.

In still a further embodiment the measuring unit is provided with a transmitting means allowing to wirelessly transmit the measured values to a computer. Herewith, the advantage can be achieved that the measured values stored in the measuring unit of the hand held device can be transferred to a computer for further data processing.

In another embodiment the measured values and/or the data processed of the measured values are displayed in one or more of the following modes:
a) distinctive levels, in particular insufficient, sufficient, good, excellent resistance;
b) numerically
c) graphically, in particular in bar-form;
d) by colors, in particular green for: good quality and red for bad quality;
e) with words, in particular good, medium, or poor bone quality; or
f) with recommendation, in particular if the bone has to be augmented before insertion of the implant.

In yet another embodiment said tool is at least partly cannulated to allow guidance by a wire placed in the central axis of said drilled hole.

A BRIEF DESCRIPTION OF THE DRAWINGS

The preferred embodiment of the invention will be described in the following by way of example and with reference to the accompanying drawings in which.

Figure 1:
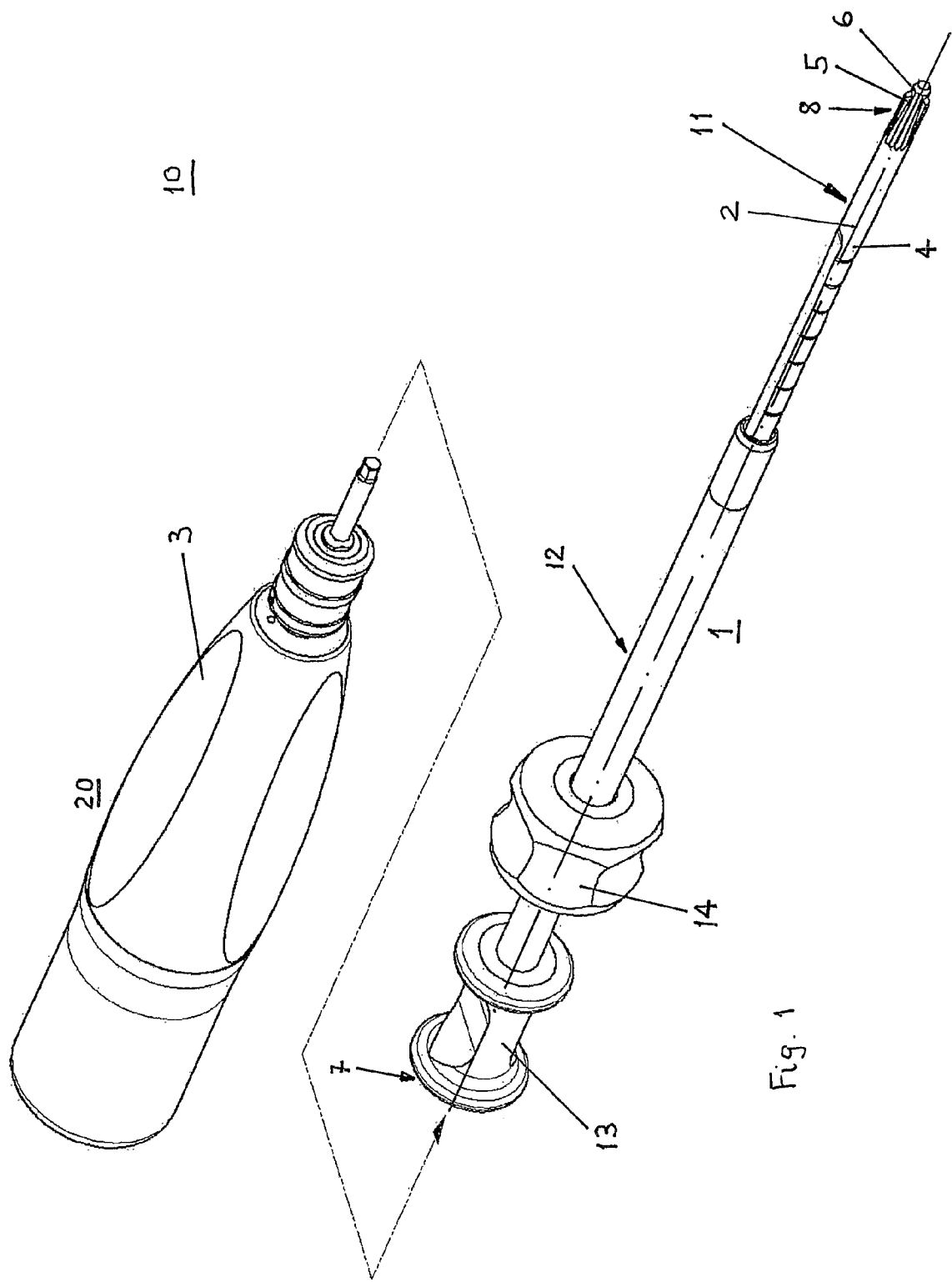
FIG. 1 illustrates one embodiment of the device according to the invention.

In FIG. 1 an embodiment of the device 10 is illustrated which comprises a tool 1 for measuring the local mechanical resistance inside of a porous body (not shown) and a measuring unit 20 comprising a handle 3. The measuring unit 20 and the tool 1 are subsequently coaxially arranged to the central axis 2 and reversibly attached to each other.

The tool 1 comprises basically three parts coaxially arranged with respect to the central axis 2. At the front of the tool 1 is a calibrated measuring tool 11 reversibly attached to the inserter 12 which is provided with a stud 13 suitable to press or hammer the measuring tool 11 into the front of the drill hole. Additionally, the tool 1 comprises an extractor ring 14 arranged between the stud 13 and the measuring tool 11 which is used to hammer out the tool 1 after the measurement has been performed.

The measuring tool 11 has a circular cylindrical shank 4 extending coaxially to the central axis 2 whereby a measuring tip 8 is disposed at the front end 6 of the tool 1. The shank 4 tapers at the measuring tip 8 toward the front end 6 in such manner that three blades 5 extending parallel to the central axis 2 are formed. When viewed in a cross-section perpendicular to the central axis 2 the three blades 5 are disposed at equal angles relative to each other.

In order to measure the mechanical resistance the blades 5 are pushed into the porous structure, e.g. the bone at the bottom of a predrilled hole to a certain distance and turned once around the central axis 2 by turning the attached measuring unit 20 and while measuring the torque exerted on the shank 4 by means of the measuring unit 20.

Figure 2:
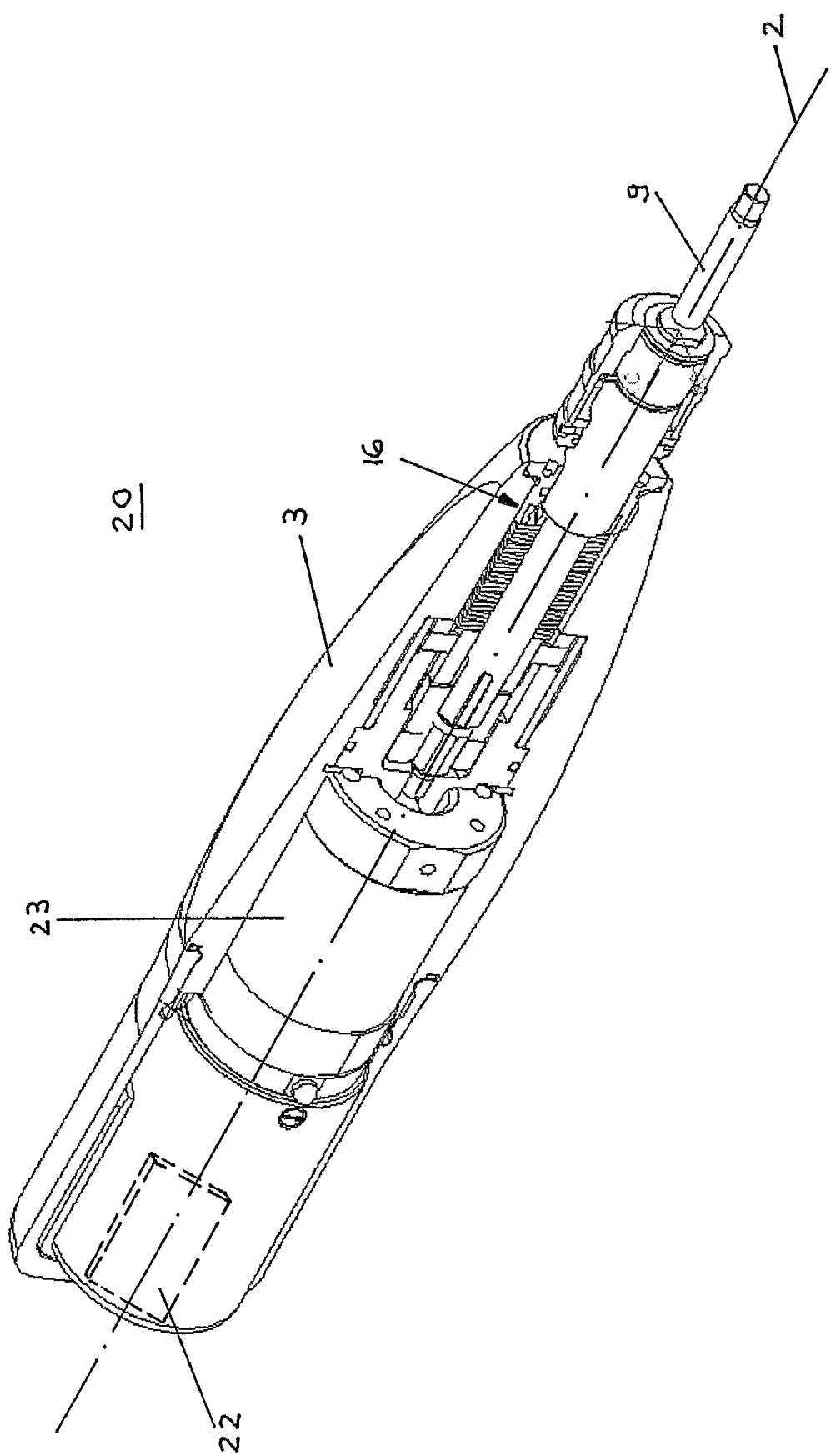
FIG. 2 illustrates one embodiment of the measuring unit of the device of FIG. 1.

As shown in FIG. 2 the measuring unit 20 is provided with a measuring means 23 apt to measure the torque applied to the shaft 9 which is connected to the shank 4 of the tool 1, conversion means (not shown), e.g. an analog-digital converter suitable to perform an analog-digital conversion of the measured values into digital data, and with a microprocessing unit 22 to retrievably store the digital data. In this particular embodiment as measuring means 23 for measuring the torque a standard torque measuring device is provided, e.g. an electrically or electromagnetically operating torque measuring device as commercially customary.

At the rear end 7 of the tool 1 (FIG. 1) the measuring unit 20 is coaxially arranged whereby the shank 4 of the tool 1 and the shaft 9 of the measuring unit 20 are coupled via e.g. a hexagon drive/socket connection. The measuring unit 20 is further provided with a torque limiting means 16 which is adjustable to a maximum value of the torque to be applied to the shank 4. An exemplary torque limiting device is disclosed in WO 01/19571 YOUNG. Additionally, the measuring unit 20 is detachable from the tool 1 and can be sterilized.

The different members of the measuring unit 20, i.e. the shaft 9, the torque limiting means 16, the measuring means 23 and the microprocessing unit 22 are subsequently coaxially arranged with regard to the central axis 2, whereby the shaft 9 forms the front of the measuring unit 20. Upon performing the measurement the tool 1 is manually rotated about the central axis 2 by turning the measuring unit 20. Furthermore, the measuring unit 20 is provided with an energy source (not shown), e.g. batteries or an accumulator.

Thus, the complete device 10 can be configured as a handheld device including a measuring unit 20 allowing a data processing and reading in-situ directly on the measuring unit 20 itself and/or the measuring unit 20 can be connected to a computer e.g. located outside of the operation room. The latter configuration allows a data processing by means of a computer inside or outside of the operation room such that the computer needs not to be sterilized. Another embodiment of the measuring device 20 can include means for wireless transmission of the measured values to a computer.

Figure 3:
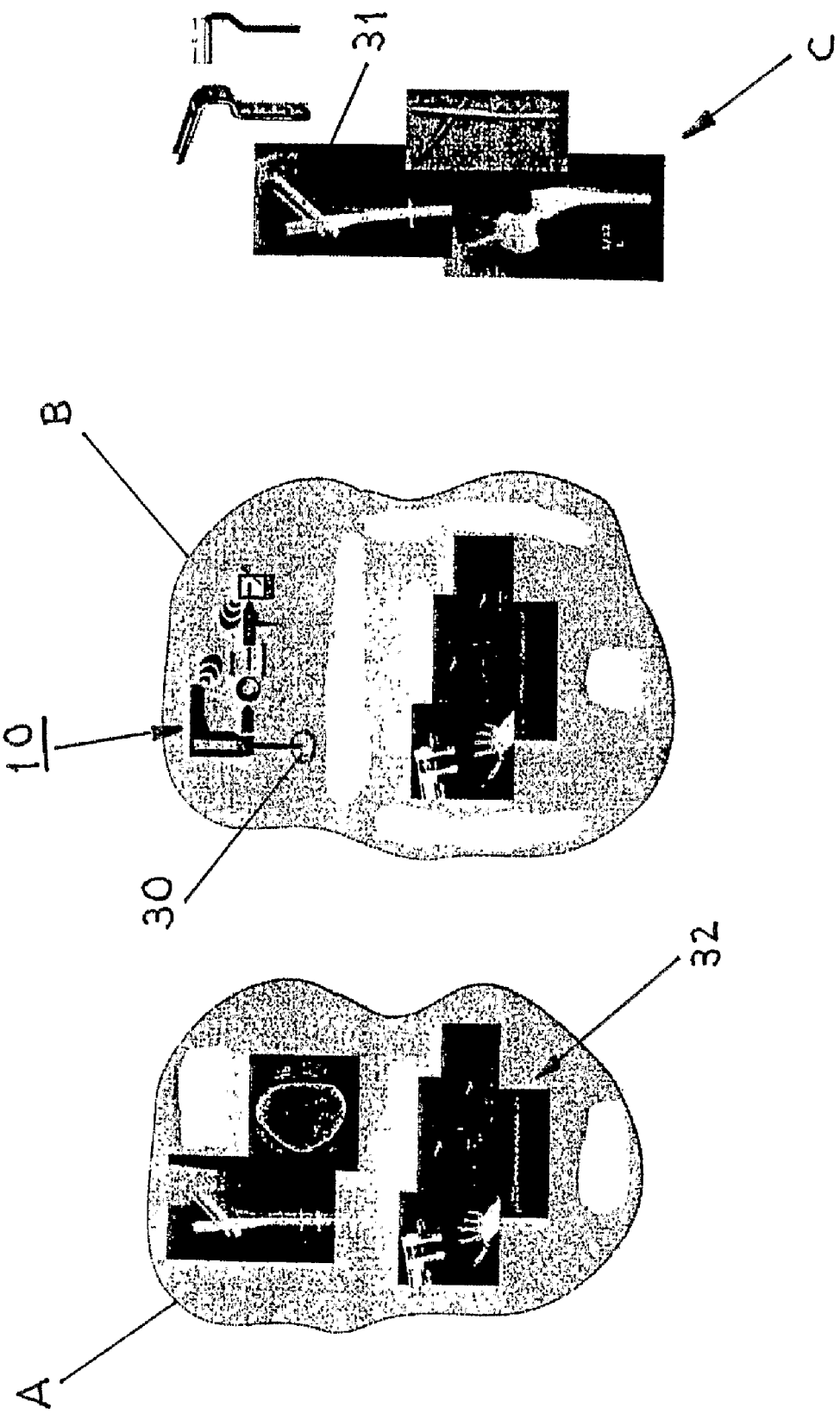
FIG. 3 illustrates a schematic representation of one application of the method according to the invention.

FIG. 3 section B exemplarily illustrates one application of the method by using the device of FIG. 1. The method described here refers to an intraoperatively determination of the local mechanical resistance inside of a porous body, i.e. a bone 30 having a variable density and/or porosity and essentially comprises the following steps:

A) selecting a site of said bone 30 destined to receive a fixation element, i.e. a bone implant 31, e.g. a bone screw;
B) drilling a hole into said bone 30;
C) measuring a mechanical parameter of the porous structure, i.e. the spongiosa of the bone 30 surrounding said drilled hole by inserting the tool 1 into said drill hole.

Exemplarily, step C can be performed by intraoperatively placing a suitable tool 1 at the site of the desired implant anchoring. In order to assess the local bone quality the tool 1 which is preferably provided with blades 5 at its front end 6 is rotated about its longitudinal axis after its insertion into the bone 30. The moment of torsion (torque) necessary for overcoming the resistance of the bone material to the rotation of the blade 5 (which by the rotation is cutting out a corresponding bone cylinder) is measured by an appropriate measuring unit 20. The measured torque can be displayed on a screen and serves as indication of the bone quality to the surgeon. In a further improved embodiment the device 10 comprises a memory in which standardized values of different bone qualities are stored which have been obtained with the same blade 5 on a variety of bones. The device 10 is able to compare the measured values with the stored values and to display the result of that comparison in different modes.

In particular, here said measuring is effected by inserting the shank 4 of said tool 1 into said hole and impacting the shank 4 with the blades 5 into said surrounding porous structure by pressing or hammering on the stud 13 of the inserter 12. The mechanical resistance is measured by pushing the blades 5 at the front end 6 of the tool 1 into the bottom of the drilled hole to a certain distance and measuring the twisting moment needed to turn the blade once around. Furthermore, here said mechanical parameter is the torsional force. The measuring is performed by continuously measuring the torque exerted on the shank 4 during one complete rotation of the tool 1 about the central axis 2. During the measuring procedure an analog-digital conversion of measured values obtained is performed by means of the measuring unit 20, the measured values as a set of measured data are recorded by means of the microprocessing unit 22 and the set of measured data is retrievably stored in the memory of the microprocessing unit 22.

Additionally, the method can comprise the further steps of:
D) comparing said measured properties with standardized values of said properties obtained with porous structures of different density of porosity;
E) displaying the result of the comparison of said measured versus said standardized properties.

The computer can be provided with software suitable for combining a plurality of parameters defining the bone quality, e.g. image based and/or physical as well as the above described mechanical parameters. By means of the different parameters the predictability of the holding resistance of the bone shall be improved.

As exemplarily shown in FIG. 3 section A the image based and or physical parameters can be obtained by means of pre- and/or intraoperative X-ray radiation and/or e.g. an ultrasonic device 32. These parameters are used to eventually replace the pre-operatively selected implant or to improve the bone quality e.g. by means of injecting bone cement as exemplarily shown in FIG. 3 section C.

What is claimed is:

1. A method for determining the local mechanical resistance inside of a porous body having a variable density and/or porosity, comprising the following steps:

A) selecting a site of said porous body destined to receive a fixation element, in particular a screw or a bone implant;

B) drilling a hole into said porous body;

C) measuring a mechanical parameter of the porous structure surrounding said drilled hole by inserting a tool having a blade into said drill hole, wherein the mechanical parameter is measured by pushing the blade into the bottom of the drilled hole to a certain distance and measuring a twisting moment needed to turn the blade once around.

2. The method according to claim 1, wherein said measuring is performed dynamically.

3. The method according to claim 1, wherein said mechanical parameter is the mechanical resistance of the porous structure due to its deformation.

4. The method according to claim 1, wherein said mechanical parameter is the mechanical resistance of the porous structure caused by the torsional force applied through rotating the tool.

5. The method according to claim 4, wherein said torsional force is measured by obtaining free axial rotation of the tool in said porous structure.

6. The method according to claim 1, wherein the twisting angle of the tool is measured which is obtained by applying a pre-selectable maximum torsional force.

7. The method according to claim 1, comprising the further steps of:

D) comparing said measured properties with standardized values of said properties obtained with porous structures of different density of porosity;

E) displaying the result of the comparison of said measured versus said standardized properties.

8. The method according to claim 1, wherein said measuring is effected by inserting said tool into said hole and impacting it into said surrounding porous structure.

9. The method according to claim 1, wherein several distinctive measurements are taken to get averaged results with standard deviation for higher accuracy.

10. The method according to claim 1, wherein several sites are selected for obtaining several values of the local mechanical resistance at this various sites.

11. The method according to claim 1, wherein the mechanical resistance is measured in the wall of said drilled hole at one or more distinctive locations.

12. The method according to claim 1, wherein a certain number of stepwise measurements are taken in one or in a number n>1 drill holes.

13. The method according to claim 12, wherein said stepwise measurements are taken by alternately predrilling to the depth planned for the next measurement and taking said measurement.

14. The according to claim 12, wherein said stepwise measurements are guided by a wire set coaxial to the central axis of the planned drill hole before the first predrilling, deep enough to stay in place during the whole measurements or even until the fixation element is inserted.

15. The method according to claim 12, wherein said stepwise measurements are used to calculate averaged results with standard deviation for each drill hole and/or in total for higher accuracy.

16. The method according to claim 12, wherein the results measured in said 1 to n drill holes are used to calculate the over all quality/strength of the fixation construct using a number m fixation elements where $m \leq n$.

17. The method according to claim 16, wherein said 1-m fixation elements are used to fix one or more additional construction elements to the porous structure.

18. The method according to claim 1, wherein the measured values are retrievably stored in a microprocessing unit.

19. The method according to claim 18, wherein the measured values retrievably stored in the microprocessing unit are transferred to a computer for further processing.

20. The method according to claim 1, wherein the hole in said porous structure is drilled at an angle between 45° and 90°, preferably between 60° and 90° with respect to the surface of the porous structure.

21. A method for determining the local mechanical resistance inside of a porous body having a variable density and/or porosity, comprising the following steps:

A) selecting a site of said porous body destined to receive a fixation element, in particular a screw;

B) drilling a hole into said porous body;

C) measuring a mechanical parameter of the porous structure surrounding said drilled hole by inserting a suitable tool into said drill hole, wherein said porous body is a surf board or part of a boat hull or any structure with foam like parts.

22. A device for measuring the local mechanical resistance inside of a porous body having a variable density and/or porosity, in particular inside of a porous bone structure comprising:

a tool with a shank designed in such a manner that it is insertable into a hole artificially drilled into said body and that it is capable of exerting a torsional force on said porous structure surrounding said drilled hole by inserting said shank of the tool into said drill hole, said shank having a central axis;

a measuring unit for determining the elastic or destructive properties of said porous body generated by the torsion force of said tool in said porous body; and displaying means for displaying the properties of said porous body determined by said measuring unit;

wherein:

the measuring unit is provided with a microprocessing unit allowing to retrievably store the measured values; and said tool is provided with blades at its front end.

* * * * *